United States Patent [19]

Haseltine et al.

[11] Patent Number: 5,204,258
[45] Date of Patent: Apr. 20, 1993

[54] GENE EXPRESSING VPT PROTEIN AND VECTORS EXPRESSING THIS PROTEIN

[75] Inventors: William A. Haseltine, Cambridge; Eric Cohen, Brighton, both of Mass.

[73] Assignee: Dana Farber Cancer Institute, Boston, Mass.

[21] Appl. No.: 360,847

[22] Filed: Jun. 2, 1989

[51] Int. Cl.$^5$ .................... C12N 1/00; C12N 1/21; C12N 15/00; C12N 15/49
[52] U.S. Cl. ........................ 530/403; 435/5; 435/69.1; 435/69.3; 435/172.3; 435/240.1; 435/320.1; 435/974; 435/252.3; 530/826; 536/23.72; 930/221; 935/9; 935/10; 935/22; 935/66
[58] Field of Search ............... 435/69.1, 252.3, 320.1, 435/240.1; 935/27, 70, 33; 536/27

[56] References Cited

U.S. PATENT DOCUMENTS 4,755,457 7/1988 Robert-Guroff et al. .............. 435/5

OTHER PUBLICATIONS

Cohen, et al., Journal of Virology, 64:3097-3099 (1990).
Cohen, et al., V. International Conference on AIDS Ontario, Canada (conference abstracts) presented Jun. 6, 1989, Abstract T.C.O. 49, p. 523.
Barre-Sinoussi, et al., Science 220:868-871 (1983).
Gallo, et al., Science 224:500-503 (1984).
Levy, et al., Science 225:840-842 (1984).
Popovic, et al., Science 224:497-500 (1984).
Sarngadharan, et al., Science 224:506-508 (1984).
Siegel, et al., N. Engl. J. Med. 305:1439-1444 (1981).
Zagury, et al., Science 231:850-853 (1986).
Ratner, et al., Nature 313:277-284 (1985).
Sanchez-Pescador, et al., Science 227:484-492 (1985).
Muessing, et al., Nature 313:450-457 (1985).
Wain-Hobson, et al., Cell 40:9-17 (1985).
Sodroski, et al., Science 231:1549-1553 (1986).
Arya, et al., Science 229:69-73 (1985).
Sodroski, et al., Science 227:171-173 (1985).
Sodroski, et al., Nature 321:412-417 (1986).
Feinberg, et al., Cell 46:807-817 (1986).
Wong-Staal, et al., AIDS Res. & Human Retroviruses 3:33-39 (1987).
Haseltine, W. A., Journal of Acquired Immune Deficiency Syndrome 1:217-240 (1988).
Guyader, et al., Nature 326:662-669 (1987).
Chakrabarti, et al., Nature 328:543-547 (1987).
J. Sodroski et al., Science 229:74-77 (1985).
P. Sonigo et al., Cell 42:369-382 (1985).
T. Jacks et al., Science 230:1237-1242 (1985).

Primary Examiner—Richard A. Schwartz
Assistant Examiner—Johnny F. Railey, II
Attorney, Agent, or Firm—David G. Conlin; Ronald I. Eisenstein

[57] ABSTRACT

Viral protein T from Human Immunodeficiency Virus Type 1 (HIV-1) is disclosed. The protein has a molecular weight of approximately 17 kD and is produced by the vpt gene of HIV-1. This protein is antigenic. Vectors capable of expressing the vpt protein are also described.

7 Claims, 8 Drawing Sheets

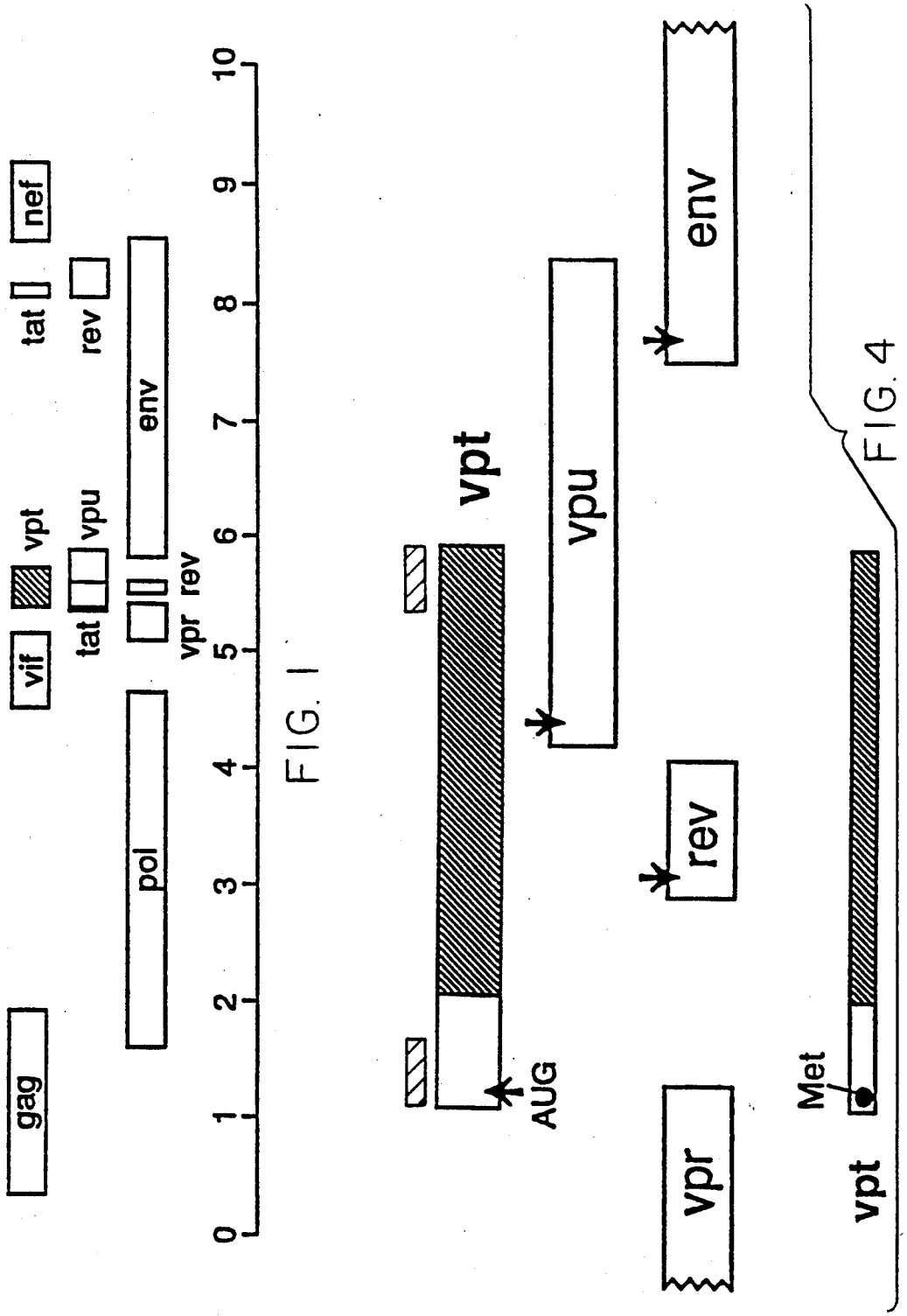

```
                                     C   A
                                    T     T
                                    T  -  A
                                    T  -  A
                                    G  -  C            ΔG = -18
                                    T  -  A
                                    T  -  A
                                    T  -  A  A  G
                                    G  -  C  C
                                    A  -  T
                                    A  -  T
                                    C  -  G  A
                                    C  -  G
                                    G  -  C
                                    T  -  A
tat  TATTGT AAAAA GT GTT GCT TTC AT TCT CCT ATG GCA GGA AGA A
          ↑
     Predicted -1 frameshift
          Cys Lys Lys Cys Cys Phe His
T    Leu •  Lys Val Leu Leu Ser
```

FIG. 3

GENE EXPRESSING VPT PROTEIN AND VECTORS EXPRESSING THIS PROTEIN

The present invention is directed to a new purified polypeptide, a vector expressing this polypeptide, a method of producing this polypeptide, an antibody to this polypeptide, and an assay for detecting in biological specimens the presence of an antibody to the antigenic determinants present in said polypeptide.

The human immunodeficiency virus (HIV-I, also referred to as HTLV-III, LAV or HTLV-III/LAV) is the etiological agent of the acquired immune deficiency syndrome (AIDS) and related disorders. [Barre-Sinoussi, et al., *Science* 220:868–871 (1983); Gallo et al. *Science* 224:500–503 (1984); Levy et al, *Science* 225:840–842 (1984); Popovic et al. *Science* 224:497–500 (1984); Sarngadharan et al, *Science* 224:506–508 (1984); Siegal et al, *N. Engl. J. Med.* 305:1439–1444 (1982)]. This disease is characterized by a long asymptomatic period followed by the progressive degeneration of the immune system and the central nervous system. Studies of the virus indicate that replication is highly regulated, and both latent and lytic infection of the CD4 positive helper subset of T-lymphocytes occur in tissue culture, [Zagury et al, *Science* 231:850–853 (1986)]. The expression of the virus in infected patients also appears to be regulated as the titer of infectious virus remains low throughout the course of the disease. Molecular virus studies of the replication and genomic organization of HIV-I show that it encodes a number of genes [Ratner et al, *Nature* 313:277–284 (1985); Sanchez-Pescador et al, *Science* 227:484–492 (1985); Meusing et al, *Nature* 313:450–457 (1985); Wain-Hobson et al, *Cell* 40:9–17 (1985)]. Three of the genes, the gag, pol and env genes are common to all retroviruses. However, the genome also encodes additional genes that are not common to most retrovirus, the tat, rev (formerly referred to as art), nef, vif, vpr and vpu genes [Sodroski et al, *Science* 231:1549–1553 (1986); Arya et al, *Science* 229:69–73 (1985); Sodroski et al, *Science* 227:171–173 (1985); Sodroski et al, *Nature* 321:412–417 (1986); Feinberg et al, *Cell* 46:807–817 (1986); Wong-Staal et al, *AIDS Res. and Human Retroviruses* 3:33–39 (1987), Haseltine, W. A., *Journal of Acquired Immune Deficiency Syndrome*, 1:217–240 (1988) which are all incorporated herein by reference.]

Nucleotide sequences from viral genomes of other retroviruses, namely HIV-II and Simian immunodeficiency virus (SIV) (previously referred to as STLV-III) also contain tat and rev regulatory sequences and show transactivation in addition to containing the structural genes. [Guyader et al, *Nature* 326:662–669 (1987); Chakrabarti et al, *Nature* 328:543–547 (1987)].

The discovery of additional HIV genes, and their expression products are important to understanding the viral life cycle. In addition, where those proteins are immunogenic, they can be used to determine presence of the HIV virus and/or stage of infection. Furthermore, such proteins can be used in developing vaccines.

SUMMARY OF INVENTION

We have now discovered a new protein expressed by cells infected with HIV, which is referred to as vpt or viral protein T. This protein has a molecular weight of approximately 17 kD and about 107 amino acids long. This protein has antigenic determinants and reacts with an antibody in vitro. A vector expressing this vpt protein contains a sufficient number of nucleotides corresponding to a region extending from the tat initiation codon and extending through the T open reading frame to express a viral protein T. Substantially all of the nucleotides corresponding to the T open reading frame are in-frame with the tat initiation codon. Accordingly, the vpt vector does not express the tat protein. Preferably, the vector will not express the rev protein.

BRIEF DESCRIPTION OF DRAWINGS

FIG. 1 is a schematic showing the genetic organization of HIV and the location of the vpt gene in relationship to other genes.

FIG. 3 is a nucleotide sequence where the −1 frameshift event occurs.

FIG. 4 is a schematic showing the product expressed by a vpt vector.

FIG. 7-2 is an autoradiogram showing immunoprecipitation of $^{35}S$ Cys labeled proteins from a vector unable to express tat because of its deletion of N terminal of tat.

FIG. 7-1 is a schematic showing two expression vectors, wherein the bottom two constructions are linearized expression vectors, and the lower one does not contain the tat initiation codon.

DETAILED DESCRIPTION OF THE INVENTION

We have now discovered that HIV encodes an additional protein and that this protein is antigenic in vitro. This protein was expressed in vitro using an in vitro generated RNA derived from an HIV provirus.

Figure 2:
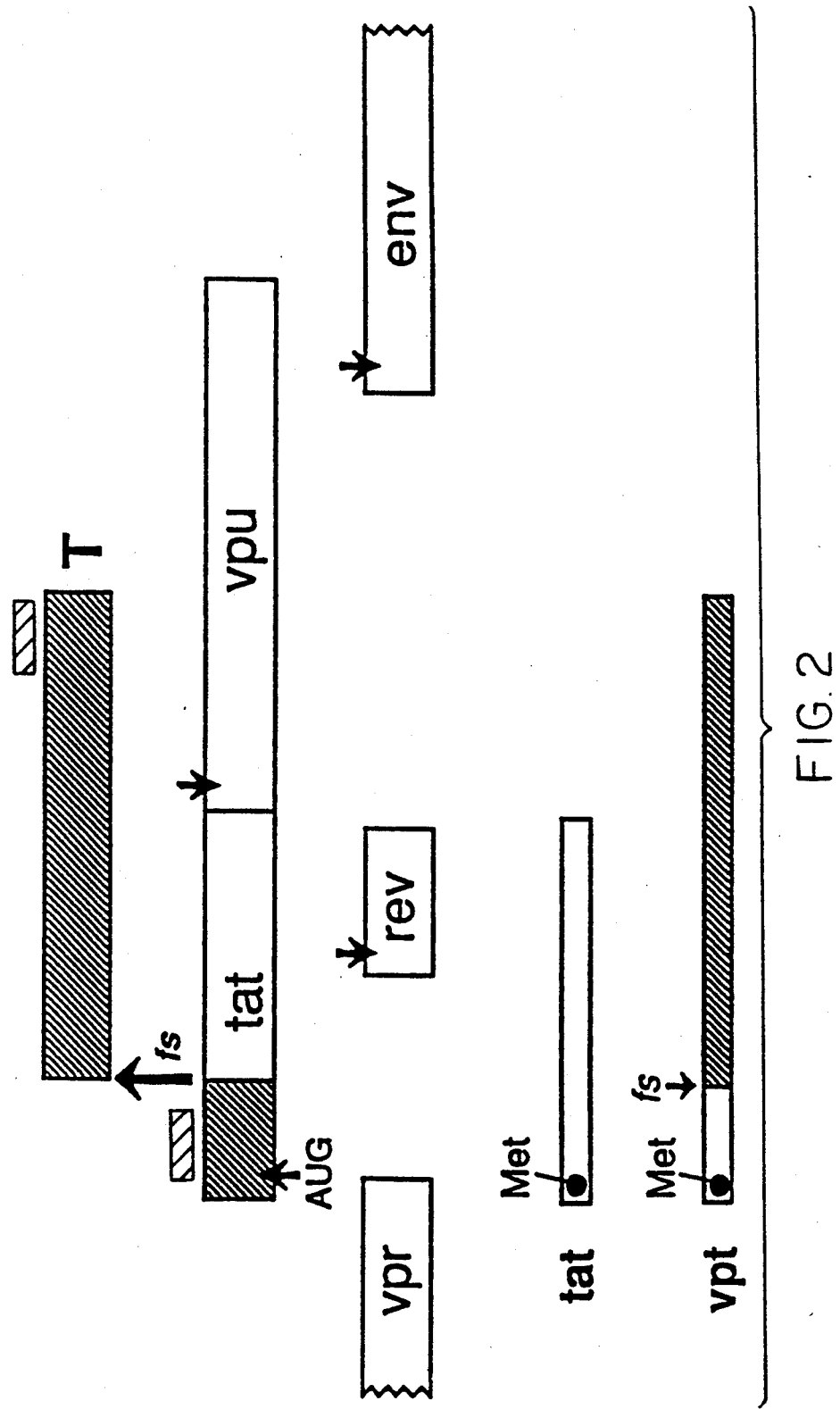
FIG. 2 is a schematic showing the shift in reading frame that occurs between the tat reading frame and the T open reading frame to produce the vpt gene.

This protein is expressed by a gene that overlaps portions of the first exons of both the tat and rev genes and requires a frame shift in its reading sequence. See FIG. 1. The 5' portion of the vpt gene is the same as the 5' portion of the tat gene and extemds through the T open reading frame [Sonigo, P. et al, *Cell* 42:369–382 (1985) which is incorporated herein be reference]. In the vpt gene, most of the T open reading frame is in the same reading frame as the tat initiation codon. Accordingly, there ia a −1 frameshift event that occurs between the tat and T open reading frame from the natural sequence to result in the vpt gene. See FIG. 2.

A vector designed to express the vpt protein will accordingly contain a nucleotide segment corresponding to a sufficient number of nucleotides extending from the first coding exon of tat through the T open reading frame to express the vpt protein. Substantially all of the nucleotides corresponding to the T open reading frame are in-frame with the tat initiation codon. Accordingly, the vpt vector will not express functional tat protein. The nucleotides preferably correspond to these regions from HIV-1.

Preferably, the −1 frameshift event from the tat initiation codon to the T open reading frame occurs in a homopolymeric region which is located at the beginning of the T open reading frame (nucleotide sequences 5455 to 5461). See FIG. 3. This region consisting of the nucleotides TAAAAAG is conserved among a wide variety of HIV strains. This frame shift can be accomplished by a variety of methods well known to the skilled artisan. For example, by interupting the homopolymeric sequence and forcing the frameshift. One can insert an additional nucleotide into this sequence. Care should be taken not to create a stop codon, however, One preferred way of constructing such a vector to result in a −1 reading frameshift in the first tat exon is by insertion of an A and replacement of an A by a G in the sequences corresponding to 5455 to 5461 to prevent too long a homopolymeric run (i.e. TAAAAG→TAAGAAAG). Other known methods of forcing a frameshift can be used based on the present disclosure. FIG. 4 shown such a vpt gene and its expression product. The vector can contain additional nucleotides corresponding to the other HIV nucleotides, but it will not contain nucleotides corresponding to the entire genome. For example, a vector can contain a region of nucleotides corresponding to nucleotides from the tat initiation codon to 126 nucleotides within the env gene. The nucleotide sequence can be RNA or DNA, but is preferably DNA. As aforesaid, because the vpt vector uses the tat initiation codon and is designed to result in a −1 frame shift event around the 5′ end of the T open reading frame, it will not produce functional tat protein.

In one embodiment, the vpt vector will not contain a sufficient number of nucleotide sequences corresponding to the second exon of tat or of rev. Preferably, the vpt vector will not contain a sufficient number of nucleotides to express at least one of the following HIV proteins as a functional protein—env, pol, rev, tat, vpu or nef. More preferably, it will not express any of them as functional protein.

The vpt protein produced is about 17 kD. The 17 kd protein typically has the amino acid sequence:

MEPVDPRLEPWKHPGSQPKTACTNCYCKKVLLSLP

SLFHNKSLRHLLWQEEAETATKSSSQQSDSSSFSIKA

VSSTCNATYTNSSNSISSSNNNSNSCVVHSNHRI.

However, some substitutions, additions, and/or deletions of these amino acids will still produce vpt protein. For example, deletion of the starting Met amino acid. Similarly, the strategy used to create the "frameshift" will affect the exact amino acids produced.

By using standard purification techniques, such as taking cell supernatant and performing size separation by a method such as sodium dodecyl sulfate-polyacrylamide gel electrophoresis (DSD-PAGE) we have been able to obtain this protein in high purity. See also FIG. 8. This protein can be purified to levels exceeding 90%, typically exceeding 95% purity.

Figure 9:
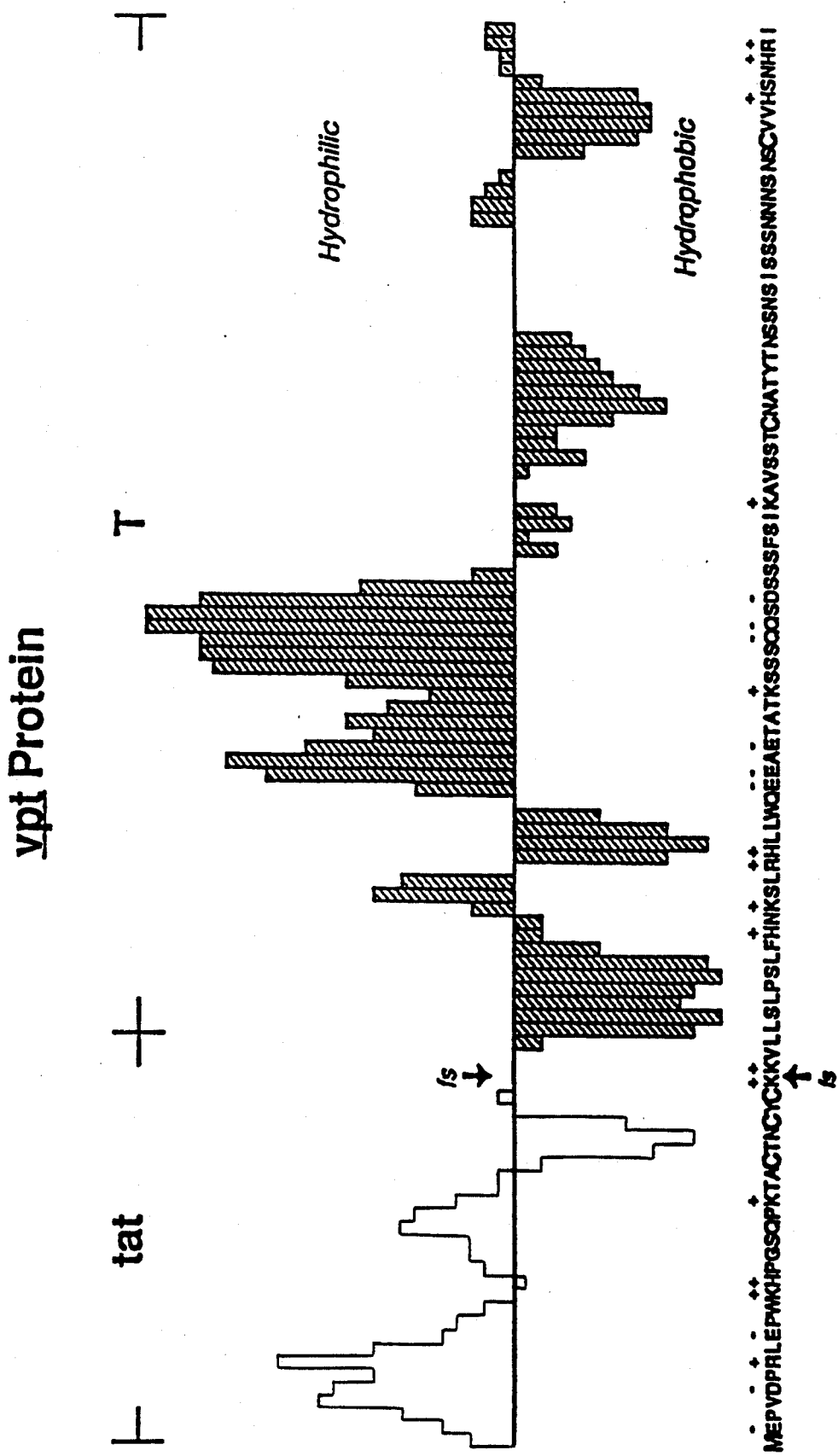
FIG. 9 is a hydrophilicity/hydrophobicity profile of the vpt protein and its predicted amino acid sequence.

This protein is antigenic. For example, an antibody directed to the N-terminal amino acids of tat will also react with the 17 kD vpt protein. However, antibodies specific for the vpt protein and not the tat gene can also be prepared. For example, an immunogenic oligopeptide corresponding in sequence to amino acid of the C-terminal portion of the vpt gene can be synthesized such as an oligopeptide corresponding to amino acids 91-106. See FIG. 9 which shows the hydrophilicity/hydrophobicity profile and expected amino acid sequence of the virus. The region where the frameshift typically occurs is shown by an arrow with the letters "fs".

This oligopeptide can be used to generate an antibody to the vpt protein. The antibody generated can be polyclonal or monoclonal depending upon the particular application for which it is designed. Such antibodies can be prepared by established techniques will known to the skilled artisan. For example, the oligopeptide can be conjugated to keyhole limpet hemocyanin (KLH) and used to raise an antibody in an animal such as rabbit. Typically, the peptide KLH conjugate is injected several times for a period of about two weeks, to generate an antibody. The antibody is then collected from serum by standard techniques. Alternatively, monoclonal antibodies can be produced in cells which produce antibodies to the protein, by using standard fusion technique for forming hybridoma calls. Typically, this involves fusing an antibody producing cell with an immortal cell line, such as a myeloma cell to produce the hybrid cell. As shown in lane (3) of FIG. 6, an antibody produced to the carboxyl end immunoprecipitated with the 17 kD protein. At this point, using patient antisera, we have not yet detected the vpt protein. This could be due to low levels of the vpt protein or possibly due to a certain stage in the viral life cycle to which such protein can readily be detected. However, it is immunogenic as it clearly reacts in vitro.

Since this protein can be used to generate an antigenic response, this protein can also be used in preparing an antigen to create a vaccine, for example, a live attenuated vaccine.

While the N-terminal region corresponds to the N-terminal portion of the tat protein (the viral protein T typically contains the same 28 N-terminal amino acids as does the tat protein), the vpt protein does not appear to have the trans-activating property of tat. Thus, it should be possible to take advantage of the substantial identity at the N-terminal region between the two proteins to block trans-activation by tat. By adding a sufficiently large amount of the protein to an HIV infected, cell, tat transactivation should be blocked. At this point, however, no inhibition of tat activity was observed during an experiment when a plasmic containing the vpt gene was cotransfected with a plasmid expressing a functional tat gene.

The vpt vector can be used in preparing a stable vpt-expressing cell line by standard techniques For example, a vpt vector containing the vpt gene, polyadenylation sequences downstream (3′) from the gene and preferably, also containing a replication origin can be used to transfect a cell. The vector also contains a promoter to permit expression of the vpt gene. Promoters contained in the vector can be any of the known promoters, and the choice is governed by the host cell used to permit expression of the desired vpt product in the hose cell of choice. Retroviral promoters are preferred. Such promoters include retroviral promoters, such as akv, SL3-3 and Friend viruses. The vector can also contain an enhancer, such enhancers are known in the art, for example, a viral enhancer. And more preferably, it contains an enhancer which is tissue specific. Preferably, the enhancer is of the same class as the promoter.

Various cell lines may differ in their ability to take up and express transfected vpt DNA. However, by us of appropriate promoters a wide range of cells can preferably be used. For example, Raji cells, HUT 78 cells, Jurkat cells, HeLa cells and NIH 3T3 cells are preferred. Human T-cells and B-cells generally are useful. Typically, mammalian cells would be preferred, but cell lines of the present invention are not limited thereto.

The vector can also contain a marker gene to aid in detection of transformed cells. This can include an antibiotic resistant gene such as the bacterial neomycin (neo) resistance genes that confer a dominant selectable resistance to the antibiotic G418 in eukaryotic cells [Southern and Berg, *J. Mol. Appl Genet.* 1:327–341 (1982)]. The vector can be used to transform cell lines, for example by being introduced into psi/2 (ecotropic) and psi AM (amphotropic) cell lines, by the calcium phosphate co-precipitation method. [Wigler, et al, *Cell* 16:777–785 (1979)]. These cell lines can constitutively produce murine leukemia virus proteins that can not package the viral transcripts [Cone, et al, *PNAS* 81:6349–6353 (1984); Mann, et al, *Cell* 33:153–159 (1983)]. Two days following transfection, cells can be selected by looking for the marker, i.e., using the antibiotic G418. G418 resistant clones are evident in 7 to 10 days. Insertion of the vpt exon does not interfere with splicing events required for transcription of neo genes. G418-resistant, psi2 and psiAM clones are isolated and clones producing large amounts of vpt protein are selected infectious units per mm are used to infect test cell. These cells are then cultured in a standard medium and harvested as needed.

Assays for the vpt protein can be prepared using standard techniques. For example, one can take a predetermined sample, i.e., the biological specimen to be tested, and add an antibody to the carboxy portion of the vpt protein. For example, a peptide corresponding to amino acids 91–106 reflects such an antigenic site. One can preferably use monoclonal antibodies. This sample is then screened to determine if there is a reaction, i.e., if a complex is formed between antibody and antigen. Alternatively, one can assay with antibodies either monoclonar or polyvalent to the antigenic determinants of the viral protein itself using known immunoassay methods, for example, using competitive immunoassays or immunometric (sandwich) assays.

The present invention is further illustrated by the following examples. These examples are provided to aid in the understanding of the invention and are not to be construed as a limitation thereof.

EXAMPLES

Figure 5:
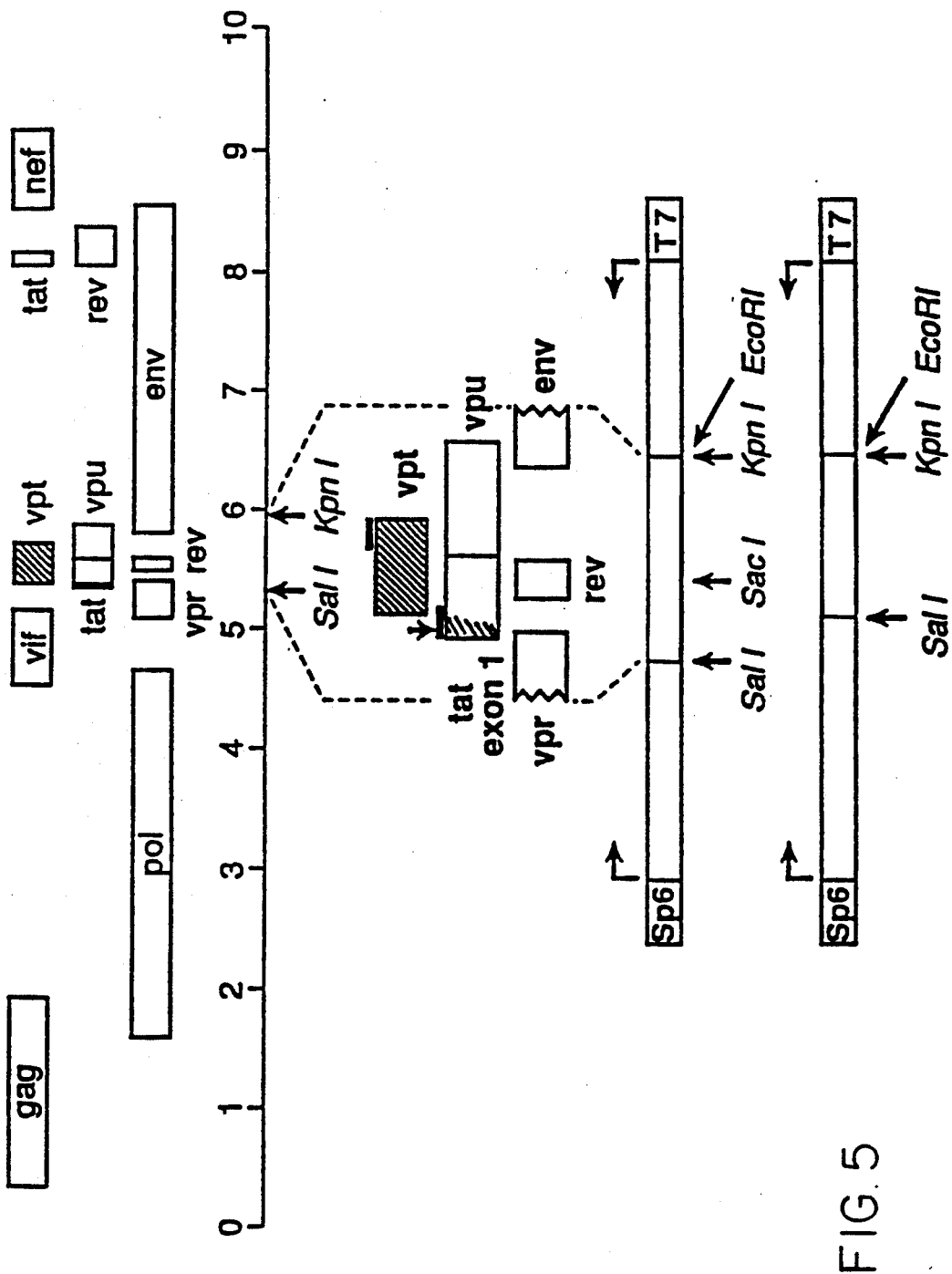
FIG. 5 is a schematic showing two expression vectors, wherein the bottom two constructions are linearized expression vectors and the lower one does not contain the tat initiation codon.

The ability of the vpt gene to encode a protein was examined by programming an in vitro reticulocyte translation lysate [Pelham, H. P. B. et al, *Eur. J. Biochem.* 67:247–256 (1986)] with RNA synthesized in vitro using the method of Melton, D. A. et al, *Nucl. Acid Res.* 12:7035–7056 (1984). The template for the experiment was derived from a fragment of the HXBc2 provirus [Arya et al, *Science* 229:74–77 (1985)] placed 3' to the SP6 bacteriophage RNA polymerase promoter. The viral sequence present in this RNA transcript, as shown in the top vector FIG. 5, extends from the first coding exon of tat (SalI position 5331; +1=transcription initiation site) to 126 nucleotides (KPN I site 5893) within the env gene. Internal restriction sites used to linearize the plasmids are indicated. Although this segment contains much of the vpu gene, it is not capable of expressing the vpu protein as it does not contain an intact vpu initiation codon.

Proteins produced in the in vitro lysate using the RNA-derived fragment were labeled with $^{35}$S-cysteine and separated by size using SDS-PAGE. See FIG. 6. The proteins synthesized in this system are indicated in lane 1. A major protein species of a relative mass of approximately 15 kD corresponding to the produce of the first exon of tat can be detected. However, the product of the first exon of rev would only be about 25 amino acids and thus too small to be detected. The N-terminal 40 amino acids of the env gene contain only 1 Cys and it therefore takes long exposure to be detected.

The plasmid was linearized by digestion at an EcoRI site located in the polylinker 3' to the HIV$_{HXBc}$2 insert and used as a template for in vitro transcription by SP6 RNA polymerase as described [Pelletier, J. and Sonenberg, N., *Cell* 40:515–526 (1985)] except that the concentration of GTP and Cap analog m$^7$GpppG was raised to 0.2 and 1.0 mM, respectively. Messenger RNAs were labeled with [5−$^3$H]CTP and purified as described. In vitro translation of equimolar amounts of RNA (equal amounts of radioactivity) were performed in reticulocyte lysate [Pelham, H. P. B., et al, *Eur. J. Biochem.* 67:247–256 (1986)]. Incubation was done at 30° C. for 30 minutes in the presence of $^{35}$S-cysteine. Labeled products were analyzed directly by 15% SDS-PAGE or immunoprecipitated. [Lee, T. H., et al, *Cell* 44:941–947] beforehand with free immune rabbit serum.

Figure 6:
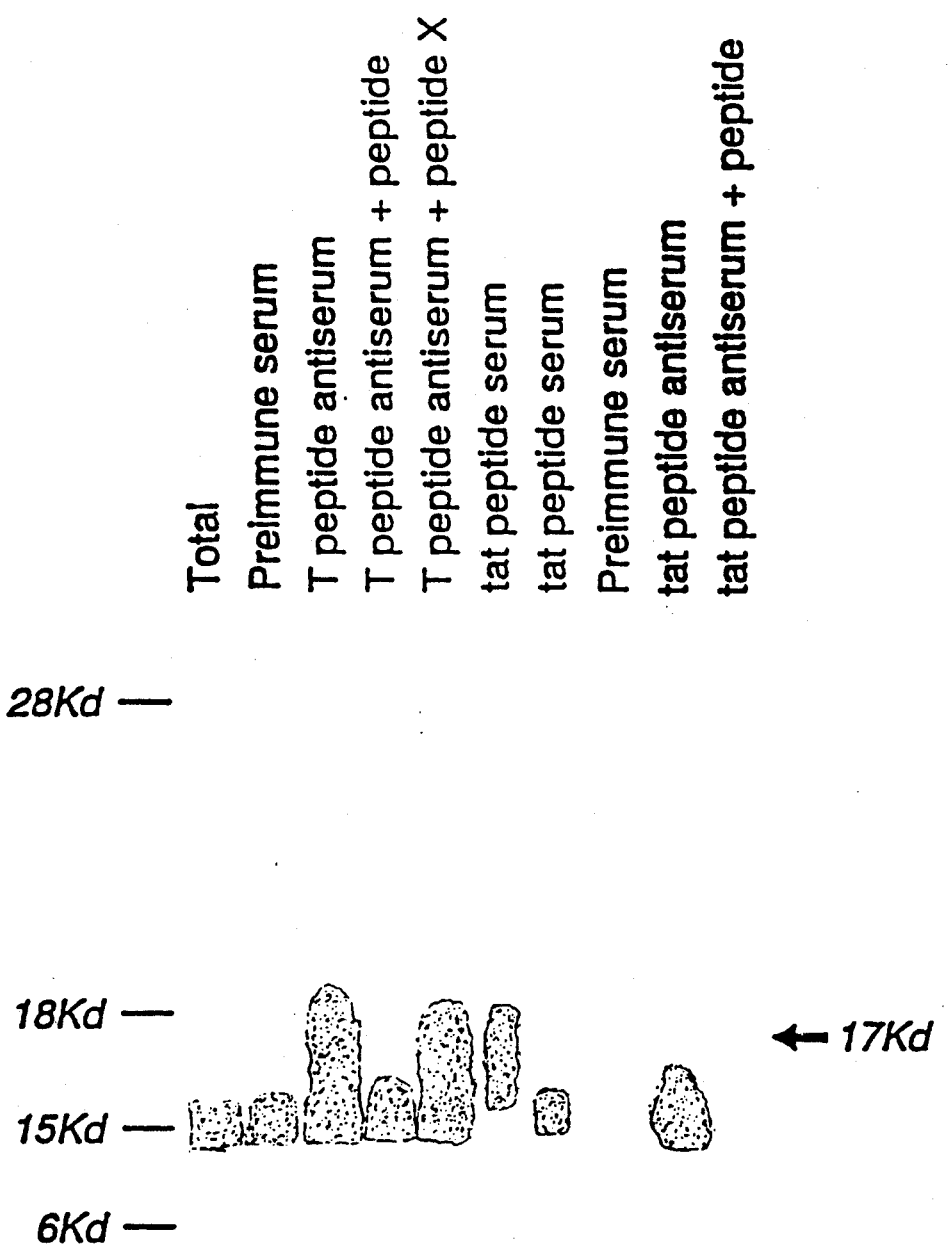
FIG. 6 are autoradiograms showing immunoprecipitation of $^{35}S$ Cys labeled proteins with anti vpt protein serum or anti tat serum.

Immunoprecipitation of the labeled lysate with anti tat anti serum is shown in lane 9 of FIG. 6. The anti tat anti serum was raised by using an oligopeptide corresponding to the first 20 amino acids of the tat protein. This amino acid sequence corresponded to the tat protein that the HXBc2 substrain of the IIIB isolet is predicted to make. The resultant peptide was conjugated to keyhole limpet hemocyanin (KLH) and used to raise antibodies in three rabbits. Multiple injection of the antigens using standard techniques was made. Thereafter, the rabbits were shown to produce antibodies that recognized the oligopeptides.

As shown in lane 9 of FIG. 6, a major protein of 15 kD is recognized by the tat antibodies. This protein corresponds to the product of the first exon of tat. A high molecular weight protein partially masked by the tat protein was precipitated, however, it was difficult to see the bands.

These experiments indicate that the rabbit sera, directed against the N-terminal portion of the tat protein, recognizes two protein species. To insure that there was not a read-through translation of tat and vpu, an anti vpu peptide sera was added. However, there was no reactivity with the 17 kD protein detected indicating that a read-through of the TAA determination codon between tat and vpu was not happening.

Antiserum containing an antibody specific for the vpt protein but not the tat protein was prepared as follows. An oligopeptide corresponding in sequence to the predicted C-terminal portion of the vpt protein was synthesized using an oligopeptide containing amino acids 91 to 106 (See FIG. 9). This sequence was derived from the sequence of the HXBc2. The oligopeptide was conjugated to KHL and used to raise antibody in rabbit in the same manner as described above.

Using the same techniques as discussed above, another RNA template was prepared, plasmic pHSK filed with the American Type Culture Collection, 12301 Parklawn Drive, Rockville, Md. 20852, ATCC Designation 75256 on 26 June 1992. Plasmid pHSK was linearized by restriction enzyme cleavage of 56 amino acids 3' to the tat AUG codon (SacI site, position 554) and used for RNA synthesis as described above. Two proteins of approximately 14 kD and 10 kD are evident in the unfractionated extract and precipitated by the anti tat rabbit serum. No reactivity was detected with the preimmune rabbit serum and the tat peptide competed for the recognition of the two proteins.

Plasmid pHSK was linearized at an EcoR1 site in the polylinker by the method as disclosed above. RNA was made in vitro and in vitro translated in a rabbit reticulocyte lysate. Immunoprecipitations of $^{35}$S cystine labeled proteins synthesized in this system with the anti vpt peptide serum are shown in FIG. 6. A 17 kD protein is immunoprecipitated by the anti vpt antibodies (lane 3). The preimmune rabbit serum does not recognize the 17 kD protein (lane 2). FIG. 6 also shows that the peptide corresponding to the C-terminal portion of the vpt competes for the recognition of the 17 kD proteins. When solutionilized, the 17 kD precipitated by the anti T serum could be reprecipitated by the anti tat antibodies indicating that the amino terminus of the protein is comprised of amino acids specified by the 5' region of tat whereas the carboxy terminal amino acids were specified by the T open reading frame.

In FIG. 6, all three of the rabbit sera raised against the N-terminal tat peptide recognized both proteins. These two proteins are not recognized, however, by preimmune rabbit serum. The data also shows that the peptide corresponding to the N-terminal 20 amino acids of tat, also competes for recognition of both proteins. However, an unrelated peptide of the same number of amino acids did not compete. Because it is difficult to see the bands, we carried out immunoprecipitation first with anti T serum (lane 7 of FIG. 6) or T antiserum+T peptide followed by immunoprecipitation with anti tat.

The 17 kD protein is initiated by the tat ATG starting codon. This is confirmed by the use of limited Ba131 digestion of the sequence 5331 to 5462 that are coding for the first 30 amino acids of the tat protein, which results in plasmid pHSKΔtat (See FIG. 7 lower vector). The viral coding sequences present in this plasmid correspond to the T open reading frame, the first exon of the rev gene, the vpu coding frame and the N-terminal portion of the env gene, but not the 5' most nucleotides of the tat gene. Plasmid HSKΔtat was linearized at an EcoR1 site in the polylinker and transcribed in vitro, as described above. $^{35}$S cys-labeled protein synthesized in an in vitro rabbit retriculocyte lysate were immunoprecipitated with anti tat protein polyclonal serum or anti vpt protein serum. FIG. 6 confirms that tat protein was not made because the initiation codon was deleted (lane 4). Similarly, no protein was recognized by the anti vpt serum, also confirming that the gene for the 17 kD vpt protein shares a portion of its exon with the tat gene (lane 5).

Figures 2, 7:
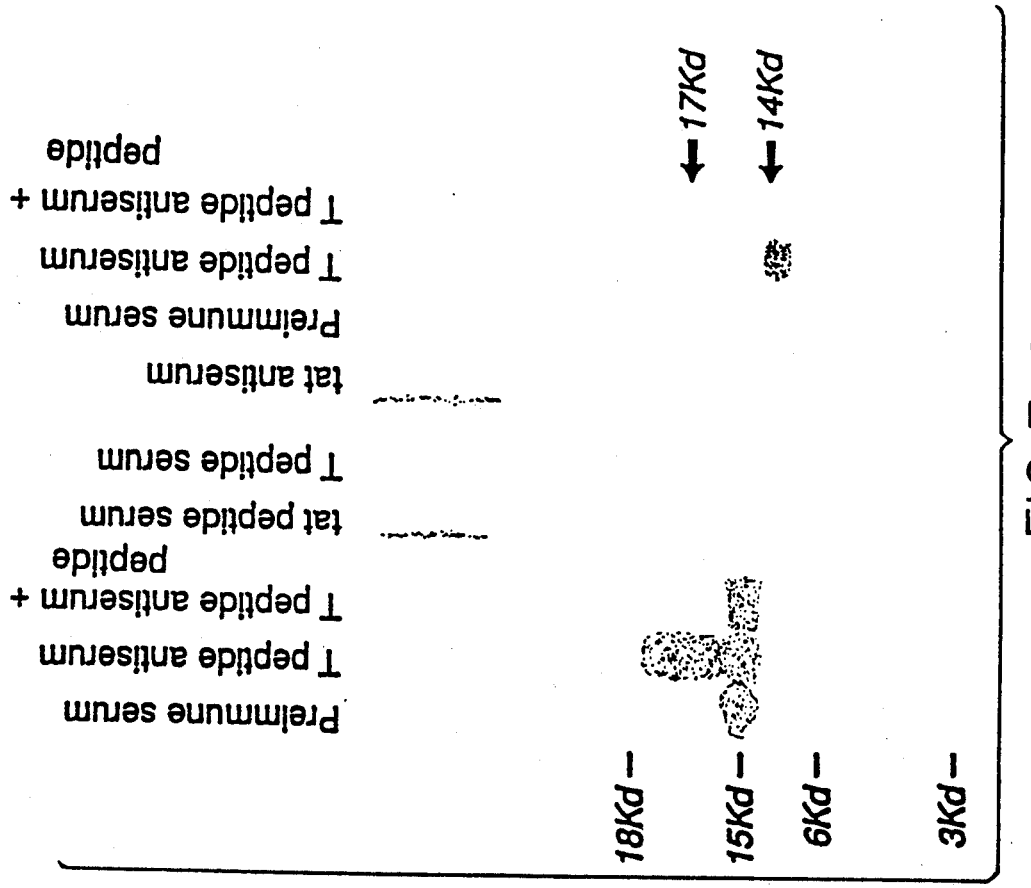
Figures 1, 7:
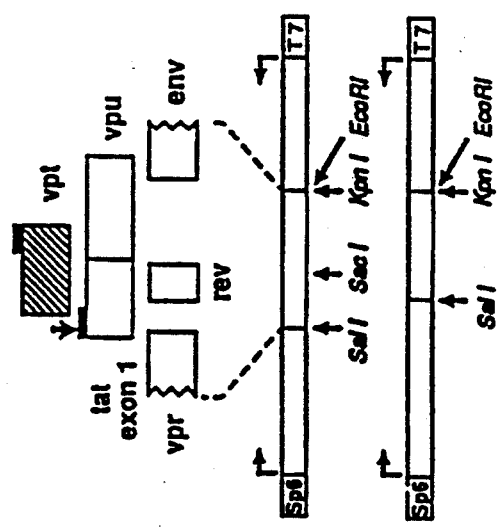

Introduction of a synthetic in-frame initiation codon at the 5' end of the T open reading frame in plasmid pHSK tat by standard techniques resulted in the expression of a protein of a molecular mass of approximately 14 kD. This protein was specifically recognized by the anti vpt protein serum as shown in FIG. 7. Because of the loss of amino terminal amino acids caused by the deletion in the 5' region of the vpt gene, the molecular weight of this protein was only 14 kD (lane 8 of FIG. 7).

These experiments suggest that in vivo a −1 ribosomal frameshift event occurs approximately 5 to 10 % of the time in this region resulting in the production of the vpt protein, rather than the tat protein.

Confirmation of the fact that the vpt protein is made by the various HIV strains can be shown by using a transcription expressor containing the viral insert from the MAL proviral clone [Alizon, M., et al, Cell 46:63-74 (1986), which incorporated herein by reference]. The template from the MAL clone spans the region between the first exon of tat and rev and the N-terminal of the env gene. In vitro translation of this RNA followed by immunoprecipitation by the method discussed above, is then performed.

A vector that would express the tat protein but not the vpt protein can be prepared by using plasmid pHSK and by site-directed mutagenesis converting the sequence TAAAAAG (5455-5461) to TAAGT. Translation of the RNA in vitro followed by immunoprecipitation with the anti tat or anti vpt serum is then performed.

Figure 8:
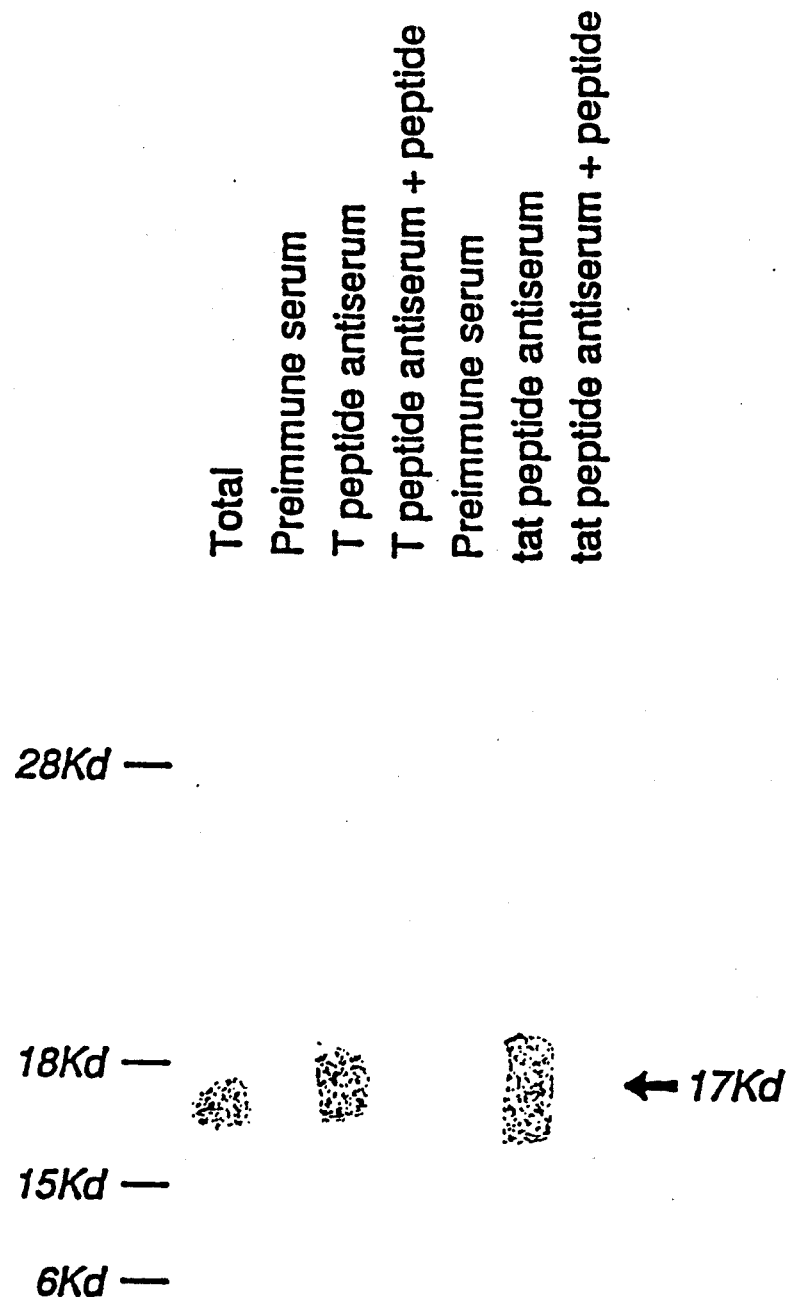
FIG. 8 are autoradiograms showing immunoprecipitation of $^{35}S$ Cys labeled proteins from a vpt vector.

Another vpt vector was also prepared using the pHSK plasmid. See FIG. 4. In this vector, using site-directed mutagenesis by standard techniques, a G nucleotide was inserted in the sequence TAAAAAG (5455-5461) to produce TAAGAAAG. The resulting plasmid was designated pHSKfs deposited with the American Type Culture Collection, 12301 Parklawn Drive, Rockville, Md. 20852, ATCC Designation 75257 on 26 June 1992. After linearization of this plasmid and translation in vitro, with the technique as discussed above, the 17 kD protein was produced but not the tat protein, as is illustrated in FIG. 8 lane (1). Immunoprecipitation of the $^{35}$S Cys-labeled protein with anti vpt protein or anti tat protein serum, specifically precipitate the 17 kD protein. (lanes 3 and 6). The peptides that were used to raise antibodies to tat and vpt, respectively competed for recognition of the 17 kD protein (lanes 4 and 7).

Stable cell lines expressing the vpt protein are produced as follows. $5 \times 10^7$ Raji cells are transfected with 10 μg of the vpt vector using the DEAE-dextran technique [Queen et al, Cell 33:741-748 (1983)]. 48 hours after transcription, the cells are labeled with $^{35}$S-cysteine and immunoprecipitated with the anti vpt serum as described above. Transformed cells are cultured by standard techniques.

It is evident that those skilled in the art, given the benefit of the foregoing disclosure, may make numerous modifications thereof and departures from the specific embodiments described herein, without departing from the inventive concepts and the present invention is to be limited solely by the scope and spirit of the appended claims.

We claim:

1. A DNA segment containing a functional vpt gene but not the entire HIV genome, wherein the DNA segment will not express functional tat protein having the ability to trans-activate.

2. A vector containing:

(a) a nucleotide segment containing a sufficient number of nucleotides corresponding to a region extending from the tat initiation codon and extending through the T open reading frame of the HIV genome, to express viral protein T, wherein the T open reading frame is in the same reading frame as the tat initiation codon wherein the vector will not express functional tat protein having the ability to trans-activate, and wherein the vector does not contain the entire HIV genome; and (b) a protomer upstream of the nucleotide segment.

3. The vector of claim 2, wherein the nucleotide segment is DNA.

4. The vector of claim 2, wherein the nucleotide segment is RNA.

5. The vector of claim 3, wherein the promoter is a viral promoter and the vector also contains an enhancer and polyadenylation sequences.

6. The vector of claim 2 wherein the HIV genome is HIV-1.

7. A cell line transformed by the vector of claim 2.

* * * * *